United States Patent [19]

Moore et al.

[11] Patent Number: 4,982,034

[45] Date of Patent: Jan. 1, 1991

[54] PRODUCTION AND PURIFICATION OF T-BUTYLSTYRENE

[75] Inventors: Eric J. Moore, Carol Stream; Marc L. Kullberg, Lisle; Lori B. Lane, Windfield, all of Ill.

[73] Assignee: Amoco Corporation, Chicago, Ill.

[21] Appl. No.: 452,706

[22] Filed: Dec. 19, 1989

[51] Int. Cl.$^5$ .......................... B01D 3/10; B01D 3/34; C07C 7/05

[52] U.S. Cl. .......................... 585/435; 203/9; 203/41; 203/73; 203/80; 585/443; 585/446; 585/452; 585/804; 585/805; 585/807; 585/820

[58] Field of Search .................. 203/9, 38, 41, 73, 80, 203/DIG. 6; 585/807, 804, 805, 446, 443, 435, 452, 820

[56] References Cited

U.S. PATENT DOCUMENTS

| | | | |
|---|---|---|---|
| 2,304,728 | 12/1942 | Boyer et al. | 203/9 |
| 2,370,948 | 3/1945 | Gadwa | 203/75 |
| 3,398,063 | 8/1968 | Van Tassell | 203/9 |
| 3,631,213 | 12/1971 | Brewer | 585/445 |
| 3,647,637 | 3/1972 | Rosenwald | 203/9 |
| 3,917,732 | 11/1975 | Vrieland et al. | 585/443 |
| 4,033,829 | 7/1977 | Higgins, Jr. et al. | 203/9 |
| 4,113,787 | 9/1978 | Ward | 585/441 |
| 4,182,658 | 1/1980 | Watson | 203/9 |
| 4,376,678 | 3/1983 | Partos | 203/91 |
| 4,457,806 | 7/1984 | Grivas et al. | 203/9 |
| 4,469,558 | 9/1984 | Watson | 203/9 |
| 4,479,025 | 10/1984 | Imai | 585/441 |
| 4,541,261 | 4/1985 | Crum | 585/806 |

*Primary Examiner*—Virginia Manoharan
*Attorney, Agent, or Firm*—Reed F. Riley; William H. Magidson; Ralph C. Medhurst

[57] ABSTRACT

A process to purify t-butylstyrene from product containing substantial amounts of t-butylethylbenzene and small amounts of alkenyl-substituted styrene impurities by a combination of vacuum fractionation and vacuum evaporation in the presence a polymerization inhibitor, and treatment with a carbonaceous adsorbent. Such a product to be purified can be prepared by catalytically, oxidatively dehydrogenating over an alkaline pyrophosphate in the vapor phase t-butylethylbenzene containing about 95 wt. % or more of the p-isomer which can be made by alkylating ethylbenzene with isobutylene in a controlled manner in the presence of cooled concentrated sulfuric acid.

10 Claims, No Drawings

PRODUCTION AND PURIFICATION OF T-BUTYLSTYRENE

BACKGROUND OF THE INVENTION

This invention relates to a method of purifying t-butylstyrene and, more particularly, to a process for preparing t-butylstyrene by the controlled alkylation of ethylbenzene with isobutylene in the presence of cooled concentrated sulfuric acid to form t-butylethylbenzene containing at least about 95 wt. % of the p-isomer, oxidatively dehydrogenating the t-butylethylbenzene in the vapor phase over an alkaline pyrophosphate catalyst, and purifying the resulting mixture rich in t-butylstyrene from unreacted t-butylethylbenzene and small amounts of alkenyl-substituted styrene impurities by a combination of a vacuum fractionation and vacuum evaporation in the presence of a polymerization inhibitor, and treatment with a carbonaceous adsorbent.

Styrene and alkyl-substituted styrene production has a long history. In the past such styrenes have been made principally by thermally or catalytically dehydrogenating, for example with steam or oxygen, the corresponding ethylbenzene or alkylethylbenzene. When making an alkyl-substituted styrene from an alkyl-substituted ethylbenzene, a problem arises in regard to the alkyl substituent and care must be exercised to dehydrogenate the ethyl group with a minimum amount of cracking or dehydrogenation of the alkyl substituent. As the number of carbon atoms in the alkyl group becomes greater, for example, dehydrogenating t-butylethylbenzene, this problem becomes more severe. A number of catalysts have been suggested for the catalytic dehydrogenation of styrene and its alkyl derivatives including alkaline earth pyrophosphates as set out in U.S. Pat. No. 3,917,732.

The alkyl-substituted ethylbenzene starting material for the manufacture of the corresponding styrene, such as t-butylethylbenzene, has commonly been made by alkylating ethylbenzene. The alkylation process can produce ring isomers with the para isomer being the most desired. Different alkylation catalysts, which produce different isomer ratios, conversions, and selectivities, such as sulfuric acid, boron trifluoride, aluminum chloride, and some mixtures thereof, have been suggested for the alkylation process. Typical is the description set out in U.S. Pat. No. 3,631,213.

t-Butylstyrene is a compound which has many uses, e.g., as a chemical intermediate and as a monomer or comonomer in the production of polymeric materials. t-Butylstyrene has replaced styrene in some applications because of the desirable physical and chemical properties that result from such a substitution. In addition, there are processes in which styrene is not suitable but where t-butylstyrene functions well.

Because t-butylstyrene belongs to the same family as styrene, there are similarities in the chemistry of its preparation. There are differences also; for example, when t-butylethylbenzene is dehydrogenated in the vapor phase, particularly at higher temperature which can optimize conversion and selectivity, small amounts of dialkenylbenzene impurities are produced. Since one of the common properties of styrene and an alkenyl-substituted styrene is the tendency to polymerize whenever they are activated by chemicals or by heat, both the dialkenyl impurities and the styrene can polymerize during manufacture, purification, and polymerization.

Although some of the fractionation techniques useful in purifying styrene can be used to purify t-butylstyrene, the boiling point of t-butylstyrene is about 70° C. higher than that of styrene and the tendency for t-butylstyrene to polymerize during fractionation is much greater than that of styrene. Thus, none of the present commercial processes for purifying styrene are acceptable for the purification of t-butylstyrene.

As written above, some of the differences between styrene and t-butylstyrene derive from compounds of the dialkenylbenzene family which are present in larger amounts in t-butylstyrene than in styrene. These cross-linking compounds can polymerize to give a type of polymer that interferes with the operation of the purification process and equipment. The crosslinked polymer has a tendency to collect in the equipment and to resist attempts to dissolve it, and even small amounts can represent a severe problem in the commercial production, purification, and polymerization of t-butylstyrene.

Some other differences from styrene that arise during separation of t-butylstyrene from impurities into a pure product derive from the presence of the ring isomers of t-butylstyrene and t-butylethylbenzene. Both meta and para isomers are found in commercial t-butylethylbenzene and in the t-butylstyrene formed from it. The m-(t-butyl)styrene has a boiling point that is intermediate between the boiling points of p-(t-butyl)ethylbenzene and p-(t-butyl)styrene and is likely to be found in both the top and bottom tower cuts if a conventional distillation column is used for separating t-butylethylbenzene and t-butylstyrene. Thus, the process for making t-butylethylbenzene should be chosen to optimize production of the para isomer if p-(t-butyl)styrene is the desired product. Removing the other isomers in the purification process for t-butylstyrene can be both inconvenient and expensive.

In application Ser. No. 646,266, filed Aug. 31, 1984, an extractive distillation process is disclosed for the separation of t-butylstyrene from an oxidative dehydrogenation reactor effluent containing t-butylethylbenzene and t-butylstyrene using anhydrous sulfolane as solvent. This process is said to work well but the use of reduced pressure and elevated temperature contribute considerably to the costs of the overall process. Trials with anhydrous sulfolane as solvent in liquid/liquid extraction of oxidative dehydrogenation reactor effluent indicate that pure t-butylstyrene could not be produced because anhydrous sulfolane and t-butylstyrene are completely miscible.

Preparing t-butylstyrene by oxidatively dehydrogenating t-butylethylbenzene in the vapor phase is a one-step process unlike the multistep process developed in the U.S. by Dow in the 1970's. However, oxidatively dehydrogenating t-butylethylbenzene produces several by-products (dialkenyl compounds) which are difficult but necessary to separate from t-butylstyrene. Also, the dehydrogenation process requires starting with a t-butylethylbenzene having a very high para/meta isomer ratio if the p-isomer of the alkylstyrene is desired. If the by-products could be easily separated and a high para/meta isomer t-butylethylbenzene feed used, the one-step process could considerably more economical.

Dialkenyl compounds even in concentrations as low as 200 ppm are effective crosslinking agents that cause formation of insoluble gel during purification and polymerization of the monomer resulting in an inferior polymer. In order to use the potentially more commercial one-step oxidative dehydrogenation, an effective commercial method to rid the dehydrogenation product from dialkenyl compounds as well as unreacted t-butylethylbenzene needs to be found, and, if p-(t-butyl)styrene is the desired product, t-butylethylbenzene with a high para/meta isomer ratio must be used as the starting material in the dehydrogenation step.

Now it has been found that the vapor phase dehydrogenation of t-butylethylbenzene to t-butylstyrene can be employed and run at a temperature giving good conversion and selectivity if the dehydrogenation is run oxidatively on a very high para to meta isomer ratio starting material, and, if a combination of vacuum fractionation, vacuum evaporation, and treatment with a carbonaceous adsorbent is used in the t-butylstyrene purification process to remove unreacted t-butylethylbenzene and such difficult-to-separate dialkenyl benzene compounds as isopropenylstyrene and sec-butenylstyrene.

SUMMARY OF THE INVENTION

In one aspect, the invention contained herein is a process to purify a product containing a major amount of t-butylstyrene and a minor amount of t-butylethylbenzene both of which contain at least about 95 wt. % of the p-isomer and, additionally, small amounts of alkenyl-substituted styrene impurities comprising:

distilling said product at an elevated temperature and reduced overhead pressure in the presence of a small amount of polymerization inhibitor to give a lower boiling mixture as overhead containing mostly said t-butylethylbenzene and a higher boiling mixture containing t-butylstyrene and less than about 2 wt. % of t-butylethylbenzene;

evaporating said higher boiling mixture at an elevated temperature and reduced pressure in the presence of a small amount of polymerization inhibitor to give a residue containing largely t-butylstyrene polymer and said polymerization inhibitor and an overhead product which contains more than about 98 wt. % t-butylstyrene; and treating said overhead product at about ambient temperature or lower with a carbonaceous adsorbent effective in removing essentially all of said alkenyl-substituted styrene impurities.

In another aspect, the invention contained herein is a process to produce t-butylstyrene comprising:

catalytically alkylating ethylbenzene with isobutylene by adding said isobutylene to ethylbenzene at a rate which minimizes formation of isobutylene oligomers at a temperature below about 30° C. in the presence of concentrated sulfuric acid to form t-butylethylbenzene containing at least about 95 wt. % of the paraisomer;

oxidatively dehydrogenating said t-butylethylbenzene with minor amount of oxygen admixed with a major amount of an inert gas in the vapor phase over an alkaline pyrophosphate under dehydrogenation conditions to form a product rich in t-butylstyrene which contains unreacted t-butylethylbenzene and small amounts of alkenyl-substituted styrene impurities;

distilling said product at an elevated temperature and reduced overhead pressure in the presence of a small amount of polymerization inhibitor to give a lower boiling mixture as overhead containing mostly said t-butylethylbenzene and a higher boiling mixture containing t-butylstyrene and less than about 2 wt. % of t-butylethylbenzene;

evaporating said higher boiling mixture at an elevated temperature and reduced pressure in the presence of a small amount of polymerization inhibitor to give a residue containing largely t-butylstyrene polymer and said polymerization inhibitor and an overhead product which contains more than about 98 wt. % t-butylstyrene; and treating said overhead product at about ambient temperature or lower with a carbonaceous adsorbent effective in removing essentially all of said alkenyl-substituted styrene impurities.

DETAILED DESCRIPTION OF THE INVENTION

The feed to the inventive purification process comprises t-butylstyrene, t-butylethylbenzene, and impurity amounts of such dialkenylbenzenes as isoprenylstyrene and sec-butenylstyrene. More preferably, the feed contains a major amount of t-butylstyrene, a minor amount of t-butylethylbenzene and impurity amounts of dialkenylbenzenes. More preferably, the feed contains more than about 60 wt.% of t-butylstyrene and the other components listed above. Such a feed typically comes from the catalyzed oxidative dehydrogenation of t-butylethylbenzene in the vapor phase. As t-butylethylbenzene is used to produce the t-butylstyrene, the para to meta ratio of each is the same, and for ease of purification by the method described herein, should be at least about 95 wt. % para isomer which requires making a catalyst choice in the manufacture of t-butylethylbenzene. The amount of the alkenylstyrene impurity in the feed is preferably less than about 2,000 ppm and, more preferably, less than about 1,000 ppm.

After purification, the t-butylstyrene product contains less than about 1 wt. %, more preferably, less than about 0.5 wt. % t-butylethylbenzene. The purified product also contains less than about 500 ppm, more preferably, less than about 100 ppm of alkenylstyrene impurities and is essentially colorless.

The distillation process is run in an efficient, packed fractionation column at a reduced overhead pressure, preferably less than about 100 mm of Hg, more preferably, less than about 20 mm of Hg, and at the lowest possible temperature resulting in efficient operation. To reduce polymerization of the styrenic product, a polymerization inhibitor such as 2,4-dinitrophenol, a 2,6-dinitrocresol, and the like is used. The polymerization inhibitor has to be used in an amount sufficient to reduce polymerization to a minimum, be relatively non-volatile at the temperature and pressure at which the t-butylstyrene is taken off in the evaporation procedure, and inert to the t-butylstyrene product. Most of the t-butylethylbenzene is separated overhead in this distillation procedure leaving behind in the higher boiling fraction t-butylstyrene, alkenylstyrene impurities, polymer, and the polymerization inhibitor.

The feed to the evaporator is the higher boiling mixture from the distillation and is fed into an evaporator which is run at a reduced pressure, preferably less than about 50 mm of Hg and more preferably, less than about 10 mm of Hg. Again, the temperature at which the evaporator is run is that which is the lowest possible consistent with effective operation of the evaporator. This helps reduce polymer formation in the evaporator. It is convenient and effective here to employ a wiped-film evaporator to reduce the temperature and hence further reduce polymerization. In the evaporator the t-butylstyrene is taken overhead carrying with it much of the alkenylstyrene impurities but leaving behind the polymer, polymerization inhibitor, and other heavies in the evaporator bottoms.

The product from evaporation, which can be over 99.5 wt. % of t-butylstyrene, is then treated at ambient temperature or below with a carbonaceous adsorbent to remove the alkenylstyrene impurities. Plant-matter active carbons such as Darco G-60, Calgon RB and BL, Norit A, etc., appear to function best for removing the alkenylstyrene impurities. Particularly preferred is Norit A made by the American Norite Co., which is particularly effective in removing the main dialkenylstyrene impurity, isoprenylstyrene.

The feed to the oxidative dehydrogenation step is t-butylethylbenzene made by the controlled alkylation of ethylbenzene with isobutylene in cooled concentrated sulfuric acid. The sulfuric acid should be more than about 80 wt. % and more preferably more than about 90 wt. % $H_2SO_4$. By controlled addition is meant addition of isobutylene such that it is used at a rate roughly equal to its rate of addition, a technique which leads to minimum formation of isobutylene oligomers. Isobutylene is used in about the stoichiometric amount and added below about 30° C. with adequate provision for removing reaction heat. Temperatures below about 10° C. can cause isobutylene condensation. Such a technique produces a t-butylethylbenzene product containing greater than about 90 wt. % of the p-isomer, p-(t-butyl) ethylbenzene which is separated from the reaction products by any one of a number of techniques known by those skilled in the art.

The feed to the oxidative dehydrogenation is the t-butylethylbenzene as made above. Generally it is mixed with air diluted with an inert gas such as nitrogen and passed at a temperature in the range of about 400 to about 700° C., more preferably in the temperature range about 490 to about 550° C., over an alkaline pyrophosphate such as a Periodic Group IIa pyrophosphate or the calcination product of $KFe_3H_{14}$ $(PO_4)_4 \cdot nH_2O$, as made in U.S. Ser. No. 399,308, filed Aug. 28, 1989, the contents of which are incorporated herein by reference. Preferably, the Periodic Group IIa pyrophosphate is calcium pyrophosphate. Reaction is generally accomplished in a fixed bed or fluidized bed reactor with the appropriate pressures and space velocities for the reactor type being employed, as may be understood by one skilled in the art. Partial pressure of the oxygen in the inert gas is generally low with mixtures of about 4 to about 10 mol % oxygen in the carrier gas being preferred and mixtures of about 6 to about 8 mol % oxygen in nitrogen more preferred.

The following Examples will serve to illustrate certain embodiments of the herein disclosed invention. These Examples should not, however, be construed as limiting the scope of the novel invention as there are many variations which may be made thereon without departing from the spirit of the disclosed invention, as those of skill in the art will recognize.

EXAMPLES

General

Determination of all liquid components was done on a HP 5890 GC equipped with a 60 m OV351 fused silica capillary column and a flame ionization detector.

EXAMPLE 1

A jacketed 5 L flask was equipped with an overhead stirrer, a thermometer, an isobutylene inlet port and an exit port. Ethylene glycol was circulated through the jacket to maintain the desired reaction temperature. A 1084 g portion of ethylbenzene and a 110 g portion of 98% concentrated sulfuric acid were placed in the flask and a dry 572 g portion of isobutylene was added at a rate of 520 mL/min. Care was taken to add a stoichiometric amount of isobutylene, as excess can lead to formation of triisobutylene as a side-product. The temperature was maintained at 30° C. After 8 hr water was added to quench the reaction. The organic layer was separated and dried over $CaCl_2$. The reaction mixture was analyzed by gas chromatography. Yield and conversion are set out in Table 1 below.

EXAMPLE 2

The procedure of Example 1 was repeated at 50° C. Yield and conversion are listed in Table 1 below.

EXAMPLE 3

The procedure of Example 1 was repeated at 70° C. Yield and conversion are listed in Table 1 below.

EXAMPLE 4

The procedure of Example 1 was repeated using an isobutylene feed rate of 1500 mL/min. The reaction time was reduced to 2.7 hr. Yield and conversion are listed in Table 1 below.

COMPARATIVE EXAMPLE 5

The procedure of Example 1 was repeated without controlling the temperature or rate of isobutylene addition. The reaction time was 4.5 hr. These conditions correspond to those described in Example 2 U.S. Pat. No. 3,631,213. Yield and conversion are listed in Table 1 below.

TABLE 1

Effect of Temperature and Isobutylene Addition Rate on the Preparation of t-Butylethylbenzene using Sulfuric Acid as Catalyst

| Example | Ethylbenzene Conv. (%) | t-BEB[1] as wt % of Total Product (%) | Isomer Distribution (para/meta) | Reaction Time (hr) |
|---|---|---|---|---|
| 1 | 90 | 98 | 95/5 | 8 |
| 2 | 77 | 90 | 95/5 | 8 |
| 3 | 52 | 75 | 95/5 | 8 |
| 4 | 95 | 95 | 95/5 | 2.7 |
| 5[2] | 34 | 47 | 93/7 | 4.5 |

[1]t-BEB is t-butylethylbenzene
[2]Comparative Example

EXAMPLE 6

A 4 ft by 1 in i.d. salt-bath-cooled reactor was employed in this Example. A thermocouple well (¼ in) down the center of the reactor was used to monitor the temperature of the reactor bed. The gas feed system consisted of a nitrogen and air source running through two separate flow controllers where they were mixed in the proper molar ratios to obtain 7 mol% oxygen in nitrogen. The mixture was joined with t-butylethylbenzene fed from a syringe pump just prior to entering the preheat zone which is kept above the boiling point of t-butylethylbenzene. The gaseous mixture after preheat enters the reactor and contacts the catalyst bed. The product after exiting the reactor was cooled by a water-cooled packed condenser. The liquid and gas products were analyzed by gas chromatography.

The reactor was loaded with 270 g of granular (18–40 mesh) calcium pyrophosphate. Table 2 below sets out the liquid and gas parameters used during the run. Approximately 75 lb of t-butylethylbenzene (para/meta ratio of 99.5/0.5) was run through the unit, and 62 lb of crude product was recovered. The combined composition of the crude product was 52% t-butylstyrene, 46% t-butylethylbenzene and 0.04% isopropenylstyrene.

TABLE 2 t-Butylethylbenzene Oxidative Dehydrogenation Run Parameters

| Molar Diluent Ratio (mol $N_2$/mol t-BEB) | WHSV ($hr^{-1}$) | Temp.[1] (°C.) | Gas Feed Rate (L/min) | t-BEB Feed Rate (g/min) |
|---|---|---|---|---|
| 18.1 | 0.23 | 525 | 2.9 | 1.08 |
| 17.9 | 0.33 | 530 | 4.0 | 1.50 |
| 18.5 | 0.39 | 535 | 4.8 | 1.74 |

[1]Salt bath temperatures

TABLE 3 t-Butylethylbenzene Oxidative Dehydrogenation Data

| Temp.[1] (°C.) | WHSV ($hr^{-1}$) | t-BEB Conversion (5) | t-BS[2] Selectivity (%) | $CO_x$ (%) |
|---|---|---|---|---|
| 525 | 0.23 | 62 | 87 | <8 |
| 530 | 0.32 | 58 | 87 | <7 |
| 535 | 0.39 | 57 | 87 | <7 |

[1]Salt bath temperatures
[2]t-BS is t-butylbenzene

EXAMPLE 7

Oxidative dehydrogenation reactor effluent of the type made in Example 6 was mixed with a polymerization inhibitor (2,6-dinitro-p-cresol, 5000 ppm) and admitted to an 80 tray, 2 in i.d. Oldershaw column at its midpoint at a rate of 8 mL/min. A typical feed mixture consisted of 57% t-butylethylbenzene, 42% t-butylstyrene, and 1% lights and heavies. A reflux ratio of 6:1 was employed and bottoms removal was controlled by the reboiler level. The temperature of the reboiler and overhead liquids were 144° C. and 67° C. respectively at 5 mm Hg pressure. Typically, 8.4 g/min of feed was introduced into the column with 5.3 g/min taken overhead and 3.2 g/min taken from the reboiler. Results of these distillations are set out in Table 4 below to show the effect of pressure on the separation of t-butylethylbenzene from t-butylstyrene.

The bottoms obtained from the above distillation were distilled (evaporated) using an 8 in Pope Scientific wiped-film evaporator coupled to a 15 tray, 2 in i.d. Oldershaw distillation column. The wiped-film evaporator was heated to 154° C. and operated under reduced pressure at 1 mm Hg. Feed (a typical feed consisted of 98 wt. % t-butylstyrene, 1 wt. % t-butylethylbenzene, 0.2 wt. % isopropenylstyrene, and 0.5 wt. % other heavy components including polymerization inhibitor and t-butylstyrene polymer) was introduced to the evaporator below the Oldershaw column at a rate of 8 mL/min. A reflux ratio of 1:1 was employed. Results from this distillation are set out in Table 5 below.

TABLE 4

80-Tray Column Distillation Results

| Pressure (mm Hg) | Condenser Conc. (% t-BEB/% t-BS) | Reboiler Conc. (% t-BEB/% t-BS) |
|---|---|---|
| 20 | 80/18 | 20/79 |
| 5 | 94/5 | 0.5/99 |

TABLE 5

Wiped-Film Evaporator Distillation Results

| | t-BS (%) | t-BEB (%) | IPS[1] (ppm) | Heavies (%) | Polymer (%) | APHA Color[2] |
|---|---|---|---|---|---|---|
| Feed | 98.0 | 0.8 | 1900 | 0.7 | 0.2 | >500 |
| Distillate | 98.3 | 0.96 | 1900 | <0.06 | 0.001 | 40–60 |

[1]IPS is isopropenylstyrene.
[2]Color was determined by ASTM D-1209-84.

COMPARATIVE EXAMPLE 8

An oxidative dehydrogenation reactor effluent made by the procedure of Example 6 and containing 30 wt. % t-butylstyrene, 65 wt. % t-butylethylbenzene, and 2340 ppm isopropenylstyrene was allowed to pass over a number of absorbents contained in a glass column in order to test their relative efficiency in reducing the isopropenylstyrene content of the effluent. The results are given below in Table 6.

TABLE 6

Comparison of Several Organic and Inorganic-Based Materials for IPS Adsorption

| Adsorbent | BEB (%) | TBS (%) | IPS (ppm) |
|---|---|---|---|
| None | 65 | 30 | 2340 |
| Celite | 66 | 29 | 2340 |
| Alumina | 66 | 29 | 2280 |
| Silica | 67 | 28 | 1940 |
| Norite A Carbon[1] | 67 | 29 | <10 |
| Darco G-60 Carbon[1] | 66 | 30 | 1550 |
| Calgon RB Carbon[2] | 68 | 27 | 540 |
| Calgon BL Carbon[2] | 68 | 28 | 390 |

[1]Made by American Norit Co.
[2]Made by Calgon Carbon Corp.

EXAMPLE 9

The product obtained from the wiped-film evaporator in Example 7 above was further purified using carbon adsorption. A 1 g portion of distillate and approximately 0.3 g of Norit A active carbon were allowed to stir in a 5 mL flask at room temperature for 3 hr. The mixture was filtered to remove the carbon, and the organic product was analyzed by gas chromatography. Results are set out below in Table 7.

TABLE 7

Carbon Adsorption Results

| Carbon | IPS (ppm) | APHA Color[1] |
|---|---|---|
| none | 1900 | 25 |
| Norit A | <100 | 10 |

[1]Color determination run according to ASTM D-1209-84.

What is claimed is:

1. A process to purify t-butylstyrene comprising:
   distilling a product comprising a major amount of t-butylstyrene and a minor amount of t-butylethylbenzene both of which contain at least about 95 wt. % of the p-isomer and, additional, less than about 2000 ppm of alkenyl-substituted styrenes at an elevated temperature and reduced overhead pressure in the presence of an amount of polymerization inhibitor sufficient to minimize polymerization to give a lower boiling mixture as overhead containing mostly said t-butylethylbenzene and a higher boiling mixture containing t-butylstyrene and less than about 2 wt. % of t-butylethylbenzene;
   evaporating said higher boiling mixture at an elevated temperature and reduced pressure in the presence of an amount of polymerization inhibitor sufficient to minimize polymerization to give a residue containing largely t-butylstyrene polymer and said polymerization inhibitor and an overhead product which contains more than about 98 wt. % t-butylstyrene; and treating said overhead product at about ambient temperature or lower with a carbonaceous adsorbent effective in removing essentially all of said alkenyl-substituted styrenes.

2. The process of claim 1 wherein said reduced overhead pressure is below about 10 mm of Hg and said reduced pressure is below about 2 mm of Hg.

3. The process of claim 2 wherein said higher boiling mixture contains less than about 0.5 wt. % of t-butylethylbenzene.

4. The process of claim 3 wherein said carbonaceous adsorbent is a plant-matter-active carbon.

5. The process of claim 4 wherein said polymerization inhibitor is 2,4-dinitrophenol, a 2,6-dinitrocresol or mixtures thereof.

6. A process to produce t-butylstyrene comprising:
catalytically alkylating ethylbenzene with isobutylene by adding said isobutylene to said ethylbenzene at a rate which minimizes formation of isobutylene oligomers at a temperature below about 30° C. in the presence of concentrated sulfuric acid to form t-butylethylbenzene containing at least about 95 wt. % of the para isomer;

oxidatively dehydrogenating said t-butylethylbenzene with a minor amount of oxygen admixed with a major amount of inert gas in the vapor phase over an alkaline pyrophosphate under dehydrogenation conditions to form a product comprising a major amount of t-butylstyrene and a minor amount of t-butylethylbenzene both of which contain at least about 95 wt. % of the p-isomer and small amounts, less than about 2000 ppm, of alkenyl-substituted styrenes;

distilling said product at an elevated temperature and reduced overhead pressure in the presence of an amount of polymerization inhibitor sufficient to minimize polymerization to give a lower boiling mixture as overhead containing mostly said t-butylethylbenzene and a higher boiling mixture containing t-butylstyrene and less than about 2 wt. % of t-butylethylbenzene;

evaporating said higher boiling mixture at an elevated temperature and reduced overhead pressure in the presence of an amount of polymerization inhibitor sufficient to minimize polymerization to give a residue containing largely t-butylstyrene polymer and said polymerization inhibitor and an overhead product which contains more than about 98 wt. % t-butylstyrene; and treating said overhead product at about ambient temperature or lower with a carbonaceous adsorbent effective in removing essentially all of said alkenyl-substituted styrenes.

7. The process of claim 6 wherein said reduced overhead pressure is below about 10 mm of Hg and said reduced pressure is below about 2 mm of Hg.

8. The process of claim 7 wherein said higher boiling mixture contains less than about 0.5 wt. % t-butylethylbenzene.

9. The process of claim 8 wherein said carbonaceous adsorbent is a plant-matter active carbon.

10. The process of claim 9 wherein said polymerization inhibitor is 2,4-dinitrophenol, a 2,6-dinitrocresol, or mixtures thereof.

* * * * *